(12) United States Patent
Huber et al.

(10) Patent No.: US 12,419,681 B2
(45) Date of Patent: Sep. 23, 2025

(54) DEVICE AND METHOD FOR DETERMINING A SWITCH-OFF TIME OF A MEDICAL INSTRUMENT

(71) Applicant: Aesculap AG, Tuttlingen (DE)

(72) Inventors: Christian Huber, Muehlheim (DE); Christoph Rothweiler, Donaueschingen (DE); Detlef Russ, Renningen (DE); Oliver Fugger, Ulm (DE); Raimund Hibst, Erbach (DE)

(73) Assignee: Aesculap AG, Tuttlingen (DE)

( * ) Notice: Subject to any disclaimer, the term of this patent is extended or adjusted under 35 U.S.C. 154(b) by 901 days.

(21) Appl. No.: 17/632,870

(22) PCT Filed: Aug. 6, 2020

(86) PCT No.: PCT/EP2020/072171
§ 371 (c)(1),
(2) Date: Feb. 4, 2022

(87) PCT Pub. No.: WO2021/023833
PCT Pub. Date: Feb. 11, 2021

(65) Prior Publication Data
US 2022/0280223 A1  Sep. 8, 2022

(30) Foreign Application Priority Data
Aug. 7, 2019 (DE) .......... 10 2019 121 375.4

(51) Int. Cl.
*A61B 18/14* (2006.01)
*A61B 18/00* (2006.01)

(52) U.S. Cl.
CPC ............... *A61B 18/1442* (2013.01); *A61B 2018/00601* (2013.01); *A61B 2018/0063* (2013.01);
(Continued)

(58) Field of Classification Search
CPC ............... A61B 18/12; A61B 18/1442; A61B 2018/00589; A61B 2018/00601;
(Continued)

(56) References Cited

U.S. PATENT DOCUMENTS

| 6,077,257 A | 6/2000 | Edwards et al. |
| 9,345,530 B2 | 5/2016 | Ballakur et al. |

(Continued)

FOREIGN PATENT DOCUMENTS

| CN | 107397585 A | 11/2017 |
| CN | 109069006 A | 12/2018 |

(Continued)

OTHER PUBLICATIONS

Examination Report received in European Application No. 20 754 219.2 dated Mar. 4, 2024, with translation, 10 pages.
(Continued)

*Primary Examiner* — Tigist S Demie
(74) *Attorney, Agent, or Firm* — Christopher A. Rothe; CM Law

(57) ABSTRACT

A method for determining a switch-off time of a medical instrument includes measuring the duration for which the temperature of a tissue is above 85° Celsius, preferably above 95° Celsius, calculating, preferably online, the mean temperature from the first time when 85° Celsius, preferably 95° Celsius is reached, measuring and/or calculating the energy input until 85° Celsius, preferably 95° Celsius, and preferably below 110° Celsius, preferably below 100° Celsius is reached, calculating a parameter SP, which links the above mentioned results, and switches off at a predetermined value. The method can be practiced with a medical instrument as well as an application and a storage medium.

13 Claims, 6 Drawing Sheets

(52) U.S. Cl.
CPC .............. *A61B 2018/00708* (2013.01); *A61B 2018/00791* (2013.01)

(58) Field of Classification Search
CPC .. A61B 2018/00619; A61B 2018/0063; A61B 2018/00642; A61B 2018/00666; A61B 2018/00708; A61B 2018/0072; A61B 2018/00732; A61B 2018/0075; A61B 2018/00767; A61B 2018/00791; A61B 2018/00875; A61B 2018/00886; A61B 2090/309; A61B 2505/05; A61B 2560/0266; A61B 2560/028; A61B 5/0075; A61B 5/01; A61B 5/4848; A61B 90/30

See application file for complete search history.

(56) References Cited

U.S. PATENT DOCUMENTS

| | | | |
|---|---|---|---|
| 2012/0245576 A1 | 9/2012 | Epstein et al. | |
| 2016/0022349 A1 | 1/2016 | Woloszko et al. | |
| 2016/0143684 A1* | 5/2016 | Honda ................ | A61B 18/085 606/34 |
| 2016/0166309 A1* | 6/2016 | K V ....................... | A61B 18/12 606/32 |
| 2017/0020597 A1 | 1/2017 | Ballakur et al. | |
| 2017/0105783 A1 | 4/2017 | Highsmith et al. | |
| 2017/0156797 A1 | 6/2017 | Hendriks et al. | |
| 2018/0345029 A1 | 12/2018 | Peyman et al. | |
| 2019/0082969 A1 | 3/2019 | Flaherty et al. | |

FOREIGN PATENT DOCUMENTS

| | | |
|---|---|---|
| EP | 3011924 A1 | 4/2016 |
| JP | 2001500763 A | 1/2001 |
| JP | 201641317 A | 3/2016 |
| JP | 201777463 A | 4/2017 |
| JP | 2017525429 A | 9/2017 |
| WO | 2012120498 A1 | 9/2012 |
| WO | 2016196196 A1 | 12/2016 |

OTHER PUBLICATIONS

Notice of Allowance received in Japanese Application No. 2022-507547 dated Feb. 20, 2024, with translation, 2 pages.

Search Report received in German Application No. 10 2019 121 375.4 dated Jun. 26, 2020, with translation, 11 pages.

Search Report received in International Application No. PCT/EP2020/072171 dated Nov. 12, 2020, with translation, 8 pages.

Written Opinion received in International Application No. PCT/EP2020/072171 dated Nov. 12, 2020, with translation, 15 pages.

Office Action received in Chinese Application No. 202080056150.8 dated Dec. 21, 2024, with translation, 8 pages.

\* cited by examiner

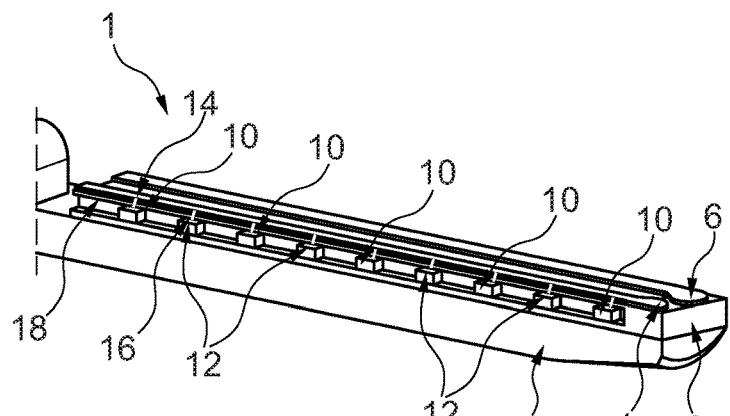
Fig. 1
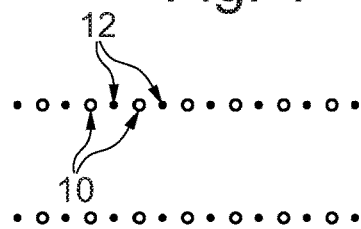
Fig. 2
Fig. 3
Fig. 4
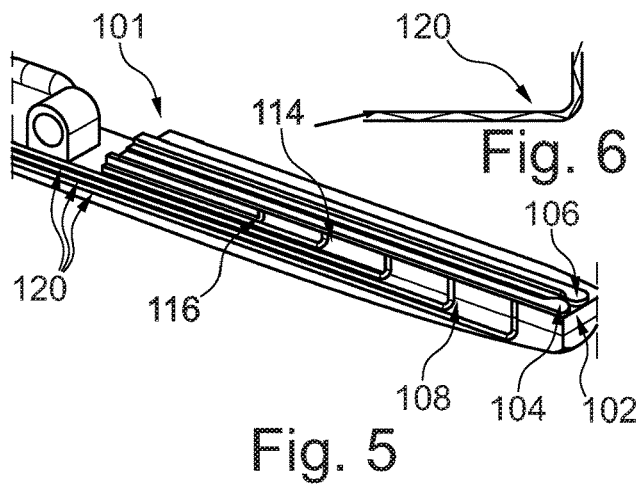
Fig. 6
Fig. 5

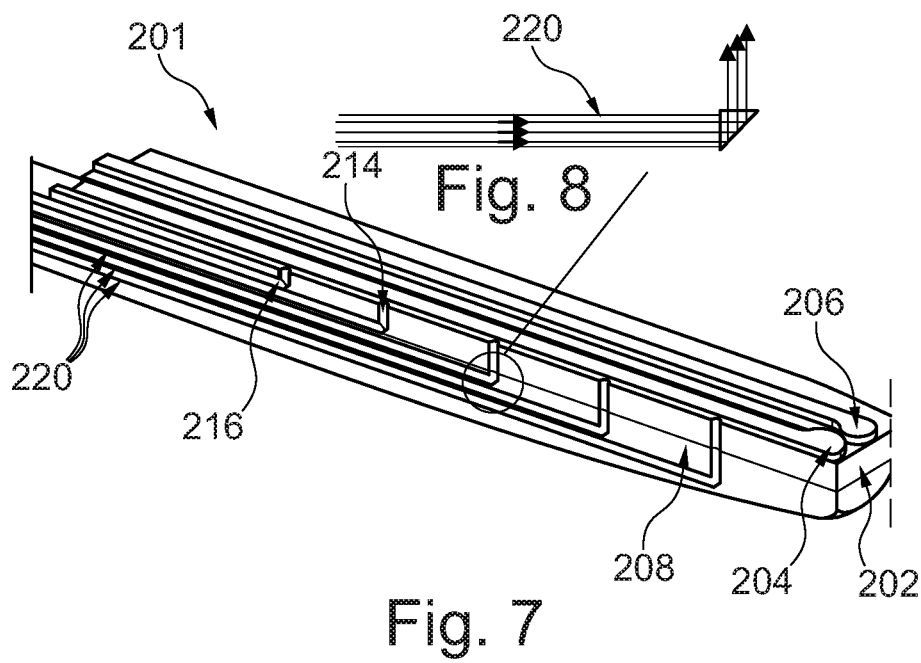
Fig. 7
Fig. 8
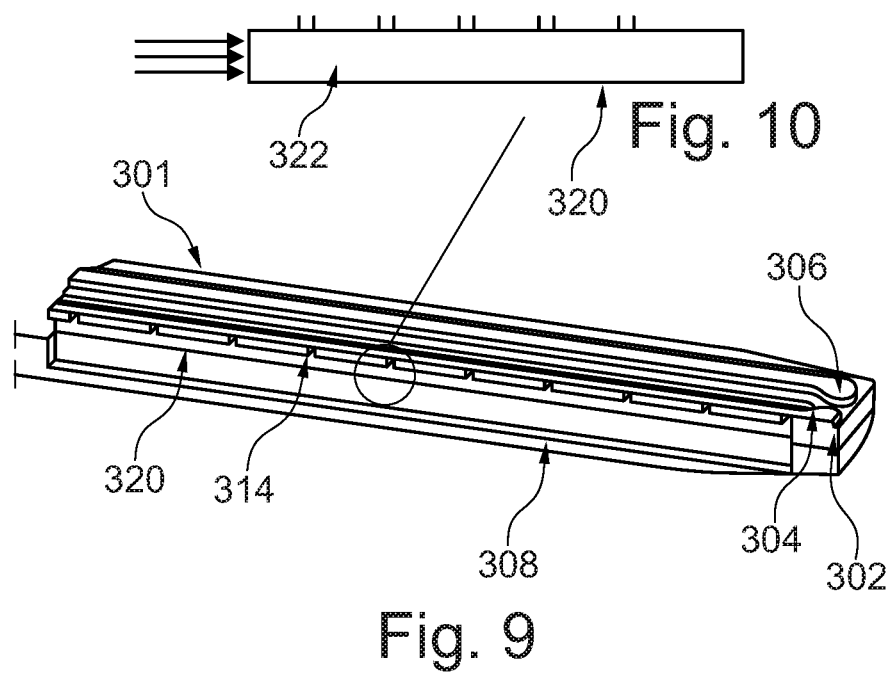
Fig. 9
Fig. 10

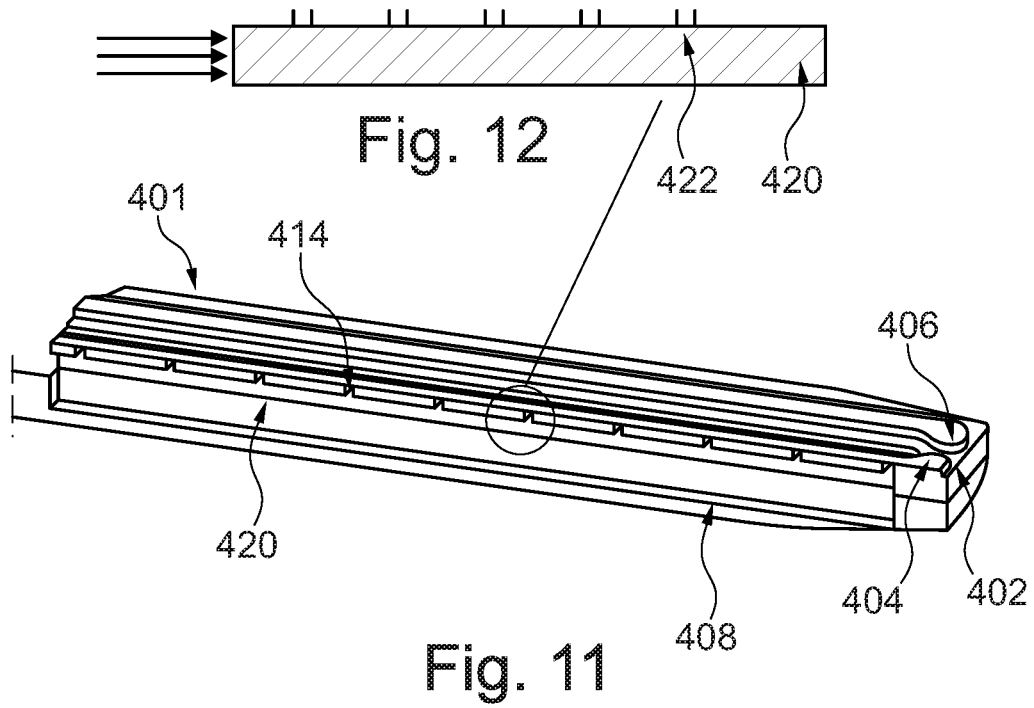
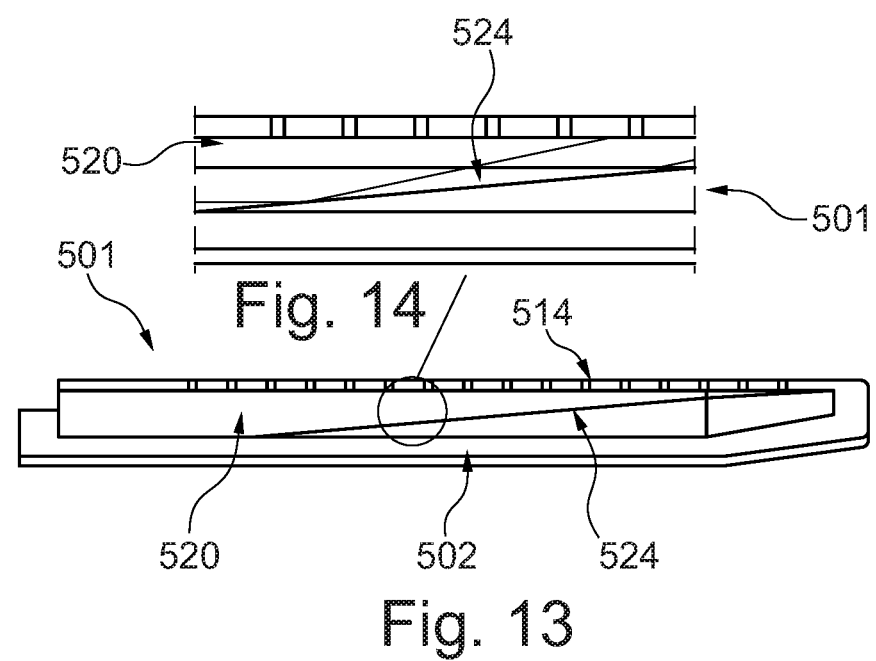

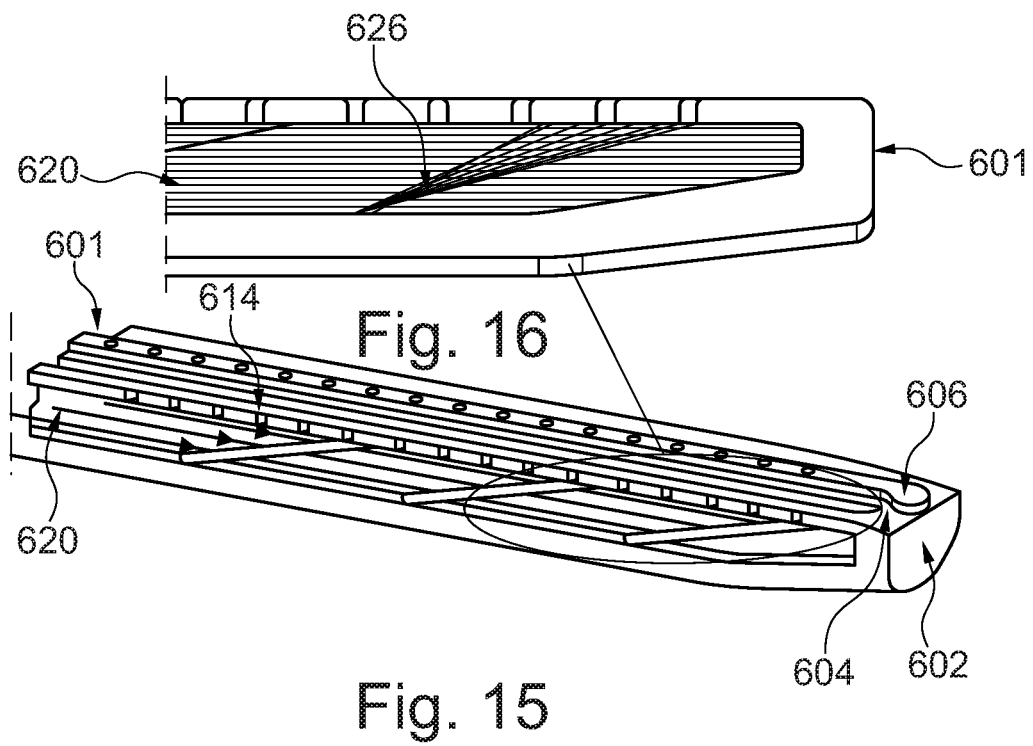
Fig. 16
Fig. 15
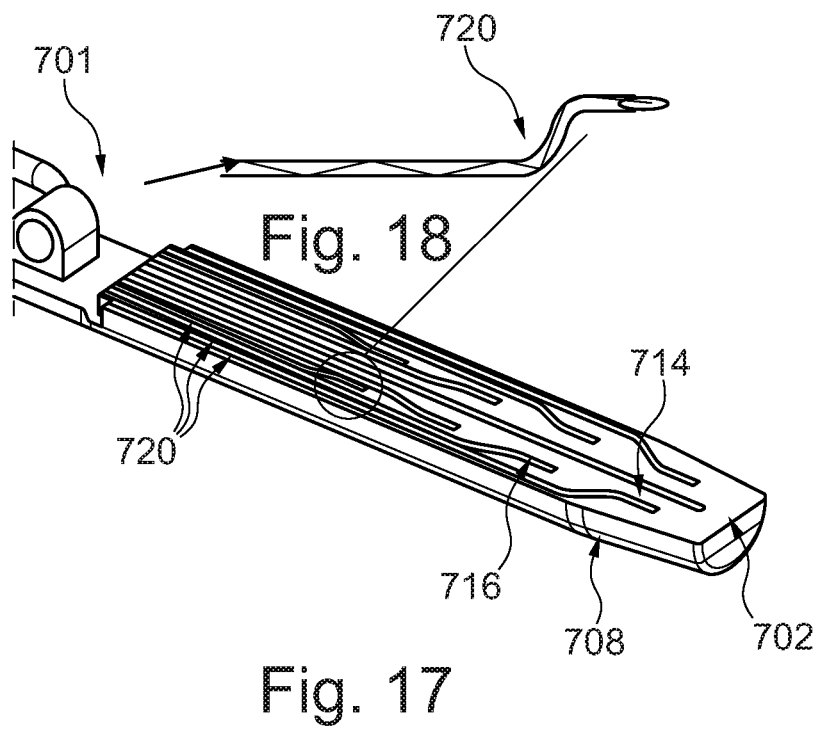
Fig. 18
Fig. 17

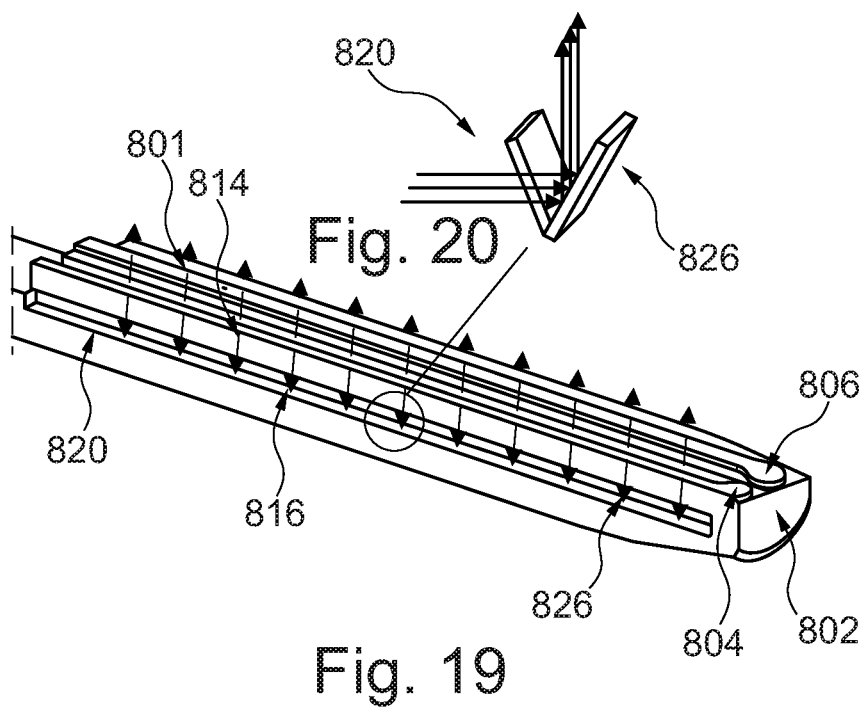
Fig. 19
Fig. 20
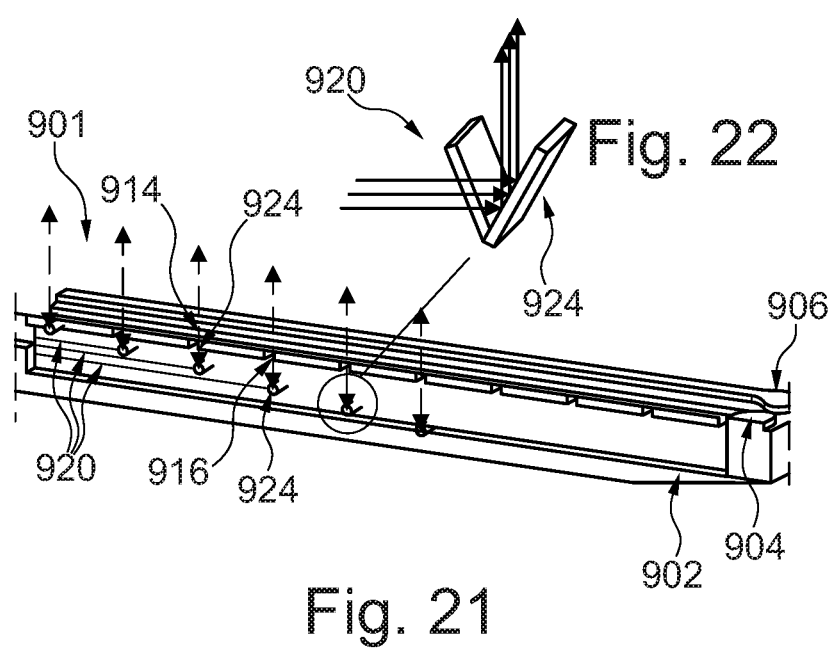
Fig. 21
Fig. 22

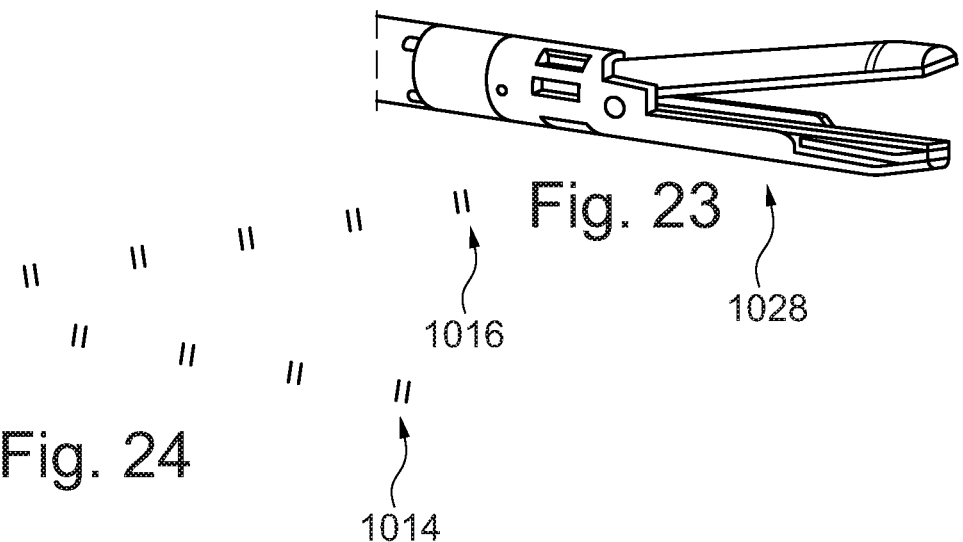
Fig. 23
Fig. 24
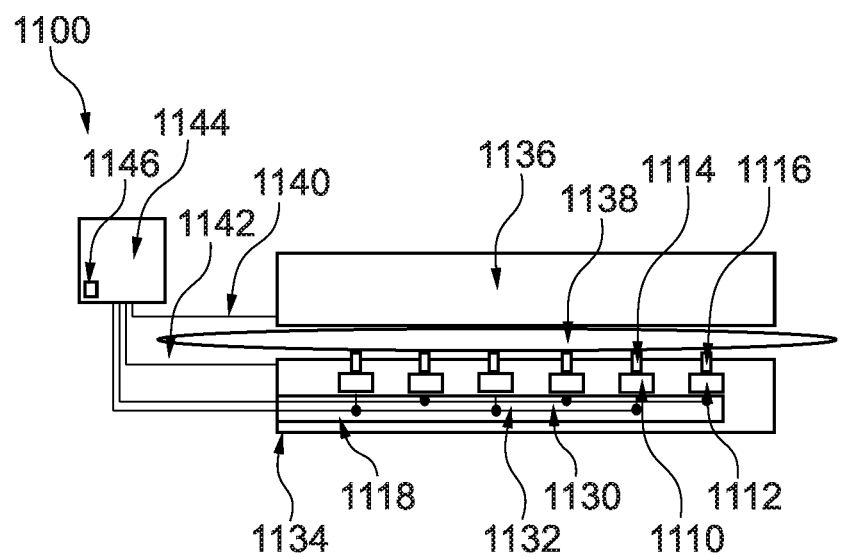
Fig. 25
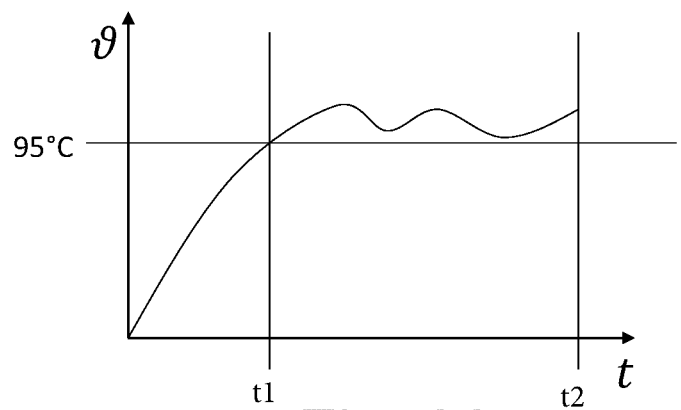
Fig. 26

DEVICE AND METHOD FOR DETERMINING A SWITCH-OFF TIME OF A MEDICAL INSTRUMENT

CROSS-REFERENCES TO RELATED APPLICATIONS

This application is the United States national stage entry of International Application No. PCT/EP2020/072171, filed Aug. 6, 2020, and claims priority to German Application No. 10 2019 121 375.4, filed Aug. 7, 2019. The contents of International Application No. PCT/EP2020/072171 and German Application No. 10 2019 121 375.4 are incorporated by reference herein in their entireties.

FIELD

The invention relates to a device and method for measuring the tissue temperature, in particular of human tissue, in a medical high-frequency surgical instrument during a thermal process (HF, ultrasound, laser instrument, etc.).

BACKGROUND

In high frequency surgery (hereinafter called HF surgery), high frequency alternating current is passed through the human body or a body part in order to selectively obliterate tissue due to the heating caused in the process (coagulation) and/or to cut it (electrotomy). The tissue damaged in this way is later resorbed by surrounding healthy tissue. An important advantage compared with conventional cutting technique with the scalpel is that simultaneously with the cut, a hemostasis by closing the vessels concerned can occur within the meaning of a coagulation. For secure closing of vessels, instruments referred to as "Seal&Cut" instruments in the trade or marketed under the trademark SEAL&CUT™ should be used. The devices used are also called an electroscalpel.

Regarding the frequencies used for the HF surgery (high frequency surgery), the body tissue behaves like an ohmic resistance (impedance). The specific resistance strongly depends on the type of tissue. The specific resistance of muscle tissue and highly perfused tissue is relatively low. That of fat is approx. by a factor of 15 higher and that of bones by a factor of 1000. Frequency, shape and level of the current must/should therefore be adapted to the type of tissue on which surgery is performed.

At present, the monopolar HF technique is most often used in the HF surgery. In that case, a pole of the HF voltage source is connected with the patient via a counter-electrode as large as possible, for example, by contacts on the operating table on which the patient is lying, by contact bracelets or contact ankle straps respectively or by adhesive electrodes. This counter-electrode is often called neutral electrode. The other pole is connected to the surgical instrument which constitutes the so-called active electrode. The current is flowing via the path of least resistance from the active electrode to the neutral electrode. In close proximity of the active electrode current density is greatest, this is where the thermal effect is strongest. The current density decreases with the square of the distance. The neutral electrode should be as large as possible, and well connected to the body so that the current density in the body is kept low and no burns occur. The skin on the neutral electrode is not noticeably heated due to the large surface. When attaching the neutral electrode, strict safety measures apply. In order not to cause any burns, the correct position and a good contact of the neutral electrode (depending on the surgical area) are crucial.

In the case of the bipolar HF technique the current, contrary to the monopolar technique, is flowing through a small portion of the body—where the surgical effect (cut or coagulation) is requested. Two electrodes insulated from each other (for example, received in instrument branches) between which the HF voltage is applied, are directly guided to the surgical site. The electric circuit is closed via the tissue located in between. Within the tissue between the electrodes the thermal effect occurs.

Coagulation clamps are known. The high frequency connections are normally provided here on handle(s). As an axis for the joint serves often a screw provided with an insulating coating with which also the two clamping legs with their handles are each pivotably attached to each other.

By means of a bipolar HF vessel sealing and/or cutting system vessels or tissue bundles can be effectively and permanently sealed in general or during cutting. Hence, the lateral thermal damage of the surrounding tissue is limited and tissue adhesions are reduced to a minimum.

In medicine, tissue is defined as an organic material which consists of a group of similarly or differently differentiated cells having a common function or structure. In addition to cells, tissue also includes the extracellular matrix (ECM). Examples of human tissues are, for example, blood vessels.

The human body consists in its chemical composition of approx. 56% oxygen (O), 28% carbon (C), 9% hydrogen (H), 2% nitrogen (N), 1.5% calcium, 1% chlorine (Cl), 1% phosphorus (P), 0.25% potassium (K), 0.2% sulfur (S) and other chemical substances in smaller proportions (all data in percent by weight).

The substance composition of the human body consists of approx. 67% water, 16% proteins (for example collagens), 10% lipids (e.g. fat), 1% carbohydrates, 1% nucleic acids and 5% various minerals (all data in percent by weight).

Collagens are a group of structural proteins (a "protein" forming a bundle of fibers) found in humans and animals, mainly of the connective tissue (more precisely: the extracellular matrix). Collagens are found, among others, in the white, inelastic fibers of tendons, ligaments, bones and cartilage. Layers of the skin (subcutaneous tissue) are also composed of collagens. In the human body, collagen is the most abundant protein, accounting for over 30% of the total mass of all proteins.

In living organisms, lipids are mainly used as structural components in cell membranes, as energy stores or as signal molecules. The term "fat" is often used as a synonym for lipids, but fats (triglycerides) are only a subgroup of lipids.

The main optical absorbers in tissues, such as, for example, in blood vessels in the NIR range, are water and collagen. The blood vessels are mostly surrounded by fat.

When electromagnetic radiation interacts with solids, liquids or gases, various effects occur, such as absorption, reflection, scattering or transmission. In other words, when electromagnetic radiation encounters an obstacle, it is either absorbed (swallowed up), scattered (deflected from its original direction), transmitted (allowed to pass through) or reflected (thrown back)—this is also referred to as remission in reflection.

In physics, remission is the diffuse (undirected) electromagnetic radiation, especially of light, which enters a scattering medium through the surface, interacts with it and exits through this surface again. This is in contrast to regular directional reflection, which satisfies the law of reflection. However, it is more common to speak of reflection in both cases. A distinction is then made between specular and diffuse reflection. In the case of remission (diffuse reflection), part of the light is absorbed and transmitted. The surface-related measure for the remission is the reflectance.

Remission spectroscopy is a branch of spectroscopy which measures the radiation remitted by a sample. Remission spectroscopy is primarily used for the spectral investigation of opaque and insoluble samples. The measured remission spectrum of a sample consists of two parts: 1) the regular reflection, where the radiation is specularly reflected from the surface. It is described by Fresnel's equations; 2) the diffuse remission, where the radiation isotropically exits the sample in all directions. It is caused by the radiation penetrating the sample and returning to the surface after partial absorption and multiple scattering.

The respective absorption spectrum of water, collagen and fat has already been measured by numerous groups. Both in the visible spectral range (VIS) and in the near infrared spectral range (NIR), the values for the absorption coefficients are available.

In the state of the art, the control processes in bipolar HF technology are controlled by the tissue impedance, which changes in the course of the energy supply, mainly due to the loss of water. The impedance of the tissue is calculated by Ohm's law using the measured voltage and current values. Due to the configuration of an instrument, the determined impedance is always an average value of the entire system (tissue, instrument, cable, generator).

The quality of the sealing of blood vessels essentially depends on the control process and the associated energy input into the tissue. In addition to overheating of the instruments, this can also result in thermal damage to the surrounding tissue. Likewise, insufficient energy input can also lead to failure/bursting of the fused sites, which in turn becomes noticeable through bleeding. Often, this bleeding does not occur until hours after the actual surgery, so that, depending on the vessel diameter, emergency surgery can be required to stop the bleeding and/or to safely close the vessel.

It is therefore known from the State of the Art to measure the tissue temperature and to incorporate the measured temperature values into the adjustment/control of the thermal processes. In order to prevent the temperature measurement results from being distorted by the electrode temperature, a sufficiently large distance and/or thermal separation/insulation is required between the tissue temperature sensor and the electrode(s). However, this is disadvantageous in that the measured tissue temperature does not correspond exactly to the tissue temperature directly at the electrode(s).

SUMMARY

The task of the invention is therefore, in addition or as an alternative to the measurement of impedance, to enable as accurate a measurement as possible of the temperature of the tissue to be fused, preferably online, in order to perform a controlled damage to the tissue immediately at the electrode(s) and, if applicable, also to prevent overheating of the instruments. In other words, it is the task of the invention to enable good coagulation by providing a switch-off criterion for switching off a medical instrument.

The task of the invention is solved by the features of patent claim 1.

The invention relates to a method for determining a switch-off time of a medical instrument, more preferably during a thermal procedure/process, comprising the following steps (preferably in this order):

Measuring the duration for which the temperature of the tissue is above 85° Celsius, preferably above 95° Celsius, and preferably below 110° Celsius, preferably below 100° Celsius (Dur95), Calculating the mean temperature as from the first time when the temperature reaches 85° Celsius, preferably 95° Celsius, and preferably below 110° Celsius, preferably below 100° Celsius, (MeanTempabTmax), Measuring and/or calculating the energy input 85° Celsius are reached, preferably 95°, and preferably below 110° Celsius, preferably below 100° Celsius, Celsius (E2Tmax), Calculating a parameter SP, which links the above mentioned results, and at a predetermined value, preferably between 2 and 3, more preferably at SP=2.5, switches off the medical instrument and/or allows it to be switched off as from this value.

A thermal process is preferably any process that generates thermal effects in the tissue by releasing energy. This also includes processes which are carried out by means of high frequency, ultrasound, laser and/or temperature. It also includes processes, which are carried out by means of high-frequency, ultrasound, laser and/or temperature instruments (for example, by means of thermocautery), and/or all medical instruments which generate thermal effects in the tissue by emitting energy.

Preferably, the method further comprises at least one of the following steps:

Emitting light, with an excitation spectrum, preferably in the VIS-/NIR range, into a tissue by means of at least one illumination, Receiving the remission of light with a remission spectrum from the tissue by at least one detector, preferably a sensor, Converting the remission spectrum by means of the detector into a detector signal, preferably an electrical signal/data signal, Sending the detector signal to a calculating unit, preferably a CPU, Calculating the remission spectrum from the detector signal by means of the calculating unit, Calculating an absorption spectrum of the tissue by comparing the excitation spectrum with the remission spectrum using the calculating unit, Calculating at least one absorption maximum from the absorption spectrum by means of the calculating unit, Calculating a temperature in the tissue by comparing the absorption maximum with at least one reference, preferably stored in the calculating unit, by means of the calculating unit, Calculating a switch-off time for a medical instrument based on temperature.

Preferably, the step of calculating a switch-off time for a medical instrument based on temperature consists of the following individual steps: measuring the duration for which the temperature of the tissue is above 85° Celsius, preferably above 95° Celsius, and preferably below 110° Celsius, preferably below 100° Celsius (Dur95), calculating the mean temperature as from the first time when 85° Celsius are reached, preferably 95° Celsius, and preferably below 110° Celsius, preferably below 100° Celsius, (MeanTempabTmax), measuring and/or calculating the energy input until 85° Celsius are reached, preferably 95°, and preferably below 110° Celsius, preferably below 100° Celsius, Celsius (E2Tmax), calculating a parameter SP, which links the above mentioned results, and switches off the medical instrument at a predetermined value, preferably between 2 and 3, more preferably at SP=2.5, and/or allows a switch-off starting from this value. In other words, the switch-off criterion can cause a direct switch-off, which means that the device actively switches off, and allows an indirect switch-off, which means that a switch-off starting from this value is passively (by another step or by a person) possible/allowed (by a program on the calculating unit).

Preferably, the duration for which the temperature of the tissue is above 85° Celsius, preferably above 95° Celsius, and preferably below 110° Celsius, preferably below 100° Celsius (Dur95), is measured by the fact that the calculating unit is calculating the temperature in the tissue and is measuring the time as from the point in time at which the temperature has reached 85° Celsius, preferably 95° Celsius, and preferably below 110° Celsius, preferably below 100° Celsius.

Preferably, the mean temperature as from the first time when 85° Celsius, preferably 95° Celsius, and preferably below 110° Celsius, preferably below 100° Celsius, (MeanTempabTmax) are reached, is calculated by the calculating unit by calculating online, preferably in real time, the average of the temperature from the first time when 85° Celsius, preferably 95° Celsius, and preferably below 110° Celsius, preferably below 100° Celsius, is reached.

Preferably, the measurement of the energy input until 85° Celsius, preferably 95° Celsius, (E2Tmax) is reached takes place by having a power meter incorporated in the medical instrument. The power meter measures the power/that is, the energy which has been consumed until the tissue reaches 95° Celsius. Alternatively or, if applicable, in addition, the power can also be determined and/or calculated on the basis of the tissue impedance or the temperature increase of the tissue over the time until the 85° Celsius, preferably 95° Celsius, is reached. The power meter can also be implicitly present in the device by means of sensors suitable for a current and voltage measurement. In other words, the calculating unit can calculate the power by means of data from a current and voltage measurement provided for this purpose.

Preferably, the parameter SP is calculated, which links the above mentioned results, and at a predetermined value, preferably between 2 and 3, more preferably at SP=2.5, switches off the medical instrument by dividing the product out of the duration for which the temperature of a tissue is above 85° Celsius, preferably above 95° Celsius, and the mean temperature as from the first time when 95° Celsius is reached, by the energy input until 85° Celsius, preferably 95° Celsius, is reached.

The parameter SP determines a favorable time for the switch-off of a medical instrument, preferably during a sealing process, more preferably during a process using instruments referred to as "Seal&Cut" instruments in the trade or marketed under the trademark SEAL&CUT™. The product of the time period/duration for which the tissue is kept above 85° Celsius, preferably above 95° Celsius, and the average temperature during this time period is divided by the energy required until 85° Celsius, preferably 95° Celsius is reached, resulting in the parameter SP. In other words: Parameter SP=(Dur95*MeanTempabTmax)/E2Tmax. As from a value of SP>2.5, the sealing process is terminated. The parameter value of >2.5 ensures that the temperature in the sealing tissue after reaching 85° Celsius, preferably 95° Celsius, and/or the time of impedance changeover for a certain time is kept above 85° Celsius, preferably above 95° Celsius, and that the control temperature is around 85° Celsius, preferably around 95° Celsius. This results in the fact that during sealing part of the water is being evaporated which is a prerequisite for successful sealing. The variable E2Tmax in the denominator of the quotient depends on the one hand on the process sequence, which has been selected for the different sealing programs, and on the other hand on the mass and composition of the tissue gripped between the electrodes. By recording the quantity, one can, in a sense, infer the heat capacity, and thus the mass in the tissue in the sealing forceps. The numerator of the equation can be interpreted as an empirical variant of the Arrhenius Formalism, according to which the degree of denaturation of tissue on exposure to heat is described in simplified form by the integral of the tissue temperature over time.

$$\Omega(t) = A \cdot \int_0^t e^{\frac{E_a}{R \cdot T(t)}} \cdot dt$$

The parameters Ea and A are tissue specific constants and R is the general gas constant. Since some, but not too much, of the tissue water must be expelled for a good sealing result, the parameter E2Tmax in the denominator is a corrective that yields a longer exposure time for large tissue volumes.

The SP parameter can be integrated into the sealing process in different ways. One possibility here is to integrate the parameter as a trigger for the switch-off process on the basis of the previous impedance switch-off criterion. In other words, the termination of sealing is released as soon as a certain value, preferably of 2, more preferably of 2.5, is exceeded.

Another possibility is to establish the parameter not as a trigger, but as a switch-off criterion. As soon as the parameter has exceeded the threshold value of 2.5, the process can be terminated. The switch-off criterion would then be independent of the impedance as a parameter for the shutdown criterion.

Preferably, the (tissue) temperature is not measured directly, but is determined by measuring another parameter (different from the temperature), which on the one hand allows a direct or indirect conclusion with respect to the current temperature (causal relationship between the temperature and the parameter) and on the other hand is (exclusively) tissue specific, i.e. is not influenced by the electrode(s). The tissue temperature is determined on the basis of at least one absorption maximum. More specifically, at least one absorption spectrum of the tissue, preferably for at least one tissue component, is determined by subtracting the remission spectrum from the excitation spectrum. Preferred tissue components are water, fat and/or collagen. From the absorption spectrum obtained in this way, it can be determined at which location at least one absorption maximum of the absorption spectrum of the tissue, preferably of at least one tissue component, is located. The absorption maximum, preferably the frequency, wavelength or position of the absorption maximum, is compared with at least one reference stored on the calculating unit, preferably on the storage medium. The at least one stored reference can then be determined from a table or by means of a reference measurement, so that it can be determined that a certain temperature prevails in the tissue at a certain position/wavelength/frequency of the absorption maximum. If this position/wavelength/frequency of the absorption maximum is not stored in a table, the temperature in the tissue can be calculated by shifting the calculated position/wavelength/frequency of the absorption maximum from a stored position/wavelength/frequency of the absorption maximum on the calculating unit. Instead of the absorption maximum, any other position/wavelength/frequency from the absorption spectrum can be used which has a significant recognition value (e.g. maxima or minima).

The tissue portions of the tissue have a typical absorption characteristic. For example, water has an absorption maximum at approx. 1470 nm at room temperature, collagen, on the other hand, has an absorption maximum at approx. 1500 nm at room temperature, and fat has an absorption maximum each at 1210 nm and at approx. 1400 nm at room temperature. Preferably, the absorption maximum of water is at 1470 nm+/−20 nm, more preferably at 1470 nm+/−10 nm, most preferably at 1470 nm+/−5 nm. Preferably, the absorption maximum of collagen is at 1500 nm+/−20 nm, more preferably at 1500 nm+/−10 nm, more preferably at 1500 nm+/−5 nm. Preferably, the absorption maximum of fat is at 1210 and at 1400 nm+/−20 nm, more preferably at 1210 and at 1400 nm+/−10 nm, more preferably at 1210 and at 1400 nm+/−5 nm.

Preferably, the method further comprises the following step:
  storing at least one reference in the form of an absorption maximum at a certain temperature in the calculating unit, preferably a storage medium in the calculating unit, preferably for water and/or fat and/or collagen.

Preferably, the calculating unit can be used to determine which temperature prevails in the tissue by using the characteristic absorption spectrum of water as a reference. It is stored on the calculating unit and/or the storage medium that water has a certain absorption maximum at a certain temperature (for example, at room temperature 1470 nm). By comparing the shift of the absorption maxima from a pre-stored value and/or by comparing with a plurality of predetermined corresponding values in a stored table, it can be determined at which wavelength of the absorption maximum which temperature prevails in the water of the tissue. The characteristic absorption spectrum of water can be determined most easily, since the tissue components in the body are known and water is the most present in the tissue with approx. 67%. Based on the measured absorption spectrum, the shift of the spectral absorption maximum of water can be calculated/determined. Based on this shift of the absorption maximum, which is approx. 0.5 nm/K, the temperature can be determined. The above is analogously applicable to fat and/or collagen and/or other components of the tissue.

The above mentioned steps for measuring the absorption spectrum can be applied analogously not only to water but also to fat, collagen or other tissue components. Thus, the individual absorption spectra of water, fat and collagen in the tissue can be determined from an absorption spectrum, which is detected by a detector and determined by a calculating unit.

Preferably, the method further comprises the following step:
  Application of the illumination and the detector to the tissue. Advantageously, the detector and the illumination are thus in direct contact with the tissue.

Preferably, the method further comprises the following step:
  Controlling and/or adjusting and/or switching off a device, preferably a medical instrument, by means of the calculating unit based on the calculated temperature and/or tissue impedance.

Preferably, the control and/or adjustment and/or switching off takes place when a predetermined temperature is reached, preferably at a temperature which is greater than 85° Celsius, preferably greater than 95° Celsius, and less than 110° Celsius, preferably less than 100° Celsius. The coagulation of tissue achieves the best result at a temperature, preferably constant temperature, above 85° Celsius, preferably above 95° Celsius, and more preferably at a temperature of less than 110° Celsius, preferably 100° Celsius.

Preferably, all steps take place online/in real time. This means that the controlling and/or adjustment and/or switching off of the medical instrument takes place online, preferably in real time. In other words, the absorption spectrum of the tissue is measured online, preferably in real time, which allows the temperature in the tissue to be calculated online, preferably in real time. The temperature will then be incorporated, preferably online, preferably in real time, into the control/adjustment of at least one electrode/sonotrode/laser source of the medical instrument, preferably a device referred to as a "Seal&Cut" instrument in the trade or marketed under the trademark SEAL&CUT™.

Preferably, the method for temperature measurement is performed during a sealing process, more preferably in the tissue in the medical instrument.

Preferably, the detectors are provided and adapted to detect remission, preferably the remission spectra in the NIR range from 1000 nm to 1700 nm, more preferably in the range from 1400 nm to 1600 nm.

Preferably, the at least one illumination and the at least one detector are spaced apart, preferably in a medical instrument.

Preferably, a method for measuring a tissue temperature is applied in a medical instrument.

Preferably, a temperature measurement device comprises a storage medium on which at least one of the following steps is stored (preferably in this order for a plurality):
  Storing at least one reference in the form of an absorption maximum at a certain temperature in the calculating unit, preferably a storage medium in the calculating unit, preferably for water and/or fat and/or collagen.
  Applying the illumination and the detector to the tissue. Advantageously, the detector and the illumination are thus in direct contact with the tissue.
  Emitting light with an illumination spectrum, preferably in the VIS-/NIR-range, into a tissue by means of at least one illumination.
  Receiving the remission of light with a remission spectrum from the tissue by at least one detector, preferably a sensor.
  Converting the remission spectrum by means of the detector into a detector signal, preferably an electrical signal/data signal.
  Sending the detector signal to a calculating unit, preferably a CPU.
  Calculating the remission spectrum from the detector signal by means of the calculating unit.
  Calculating an absorption spectrum of the tissue by comparing the illumination spectrum with the remission spectrum using the calculating unit.
  Calculating at least one absorption maximum from the absorption spectrum by means of the calculating unit,
  Calculating a temperature in the tissue by comparing the absorption maximum with at least one reference, preferably stored in the calculating unit, by means of the calculating unit.
  Controlling and/or adjusting and/or switching off a device, preferably a medical instrument, by means of the calculating unit based on the calculated temperature and/or tissue impedance.

In other words, in temperature measurement during a sealing process, remission spectra in the NIR range from 1000 nm to 1700 nm are detected online by a detector. The shift in the position of the absorption maxima, which can be derived from the recorded spectra, can be used to infer the temperature of the tissue captured in the instrument, with sufficient accuracy for the application. With increasing temperature, the position of the absorption peak shifts towards shorter wavelengths. The shift is here approx. 0.5 nm/K. If the tissue cools down further, the absorption peak shifts again towards longer wavelengths. Since the main absorber in the tissue to be sealed is water in the wavelength range around approx. 1470 nm, the temperature determined in this way reflects the temperature in the water portion of the tissue. The particular advantage of this temperature measurement method is that it can be used to measure the actual temperature in the tissue, since the NIR radiation can pass through the entire thickness of the tissue layer due to scattering. In contrast, when measuring the temperature during sealing with a thermocouple, only the temperature of the contact surface is measured. The temperature and the heat capacity of the electrodes represent a disturbance variable for the determination of the tissue temperature with this method. This leads to latency times and distortions of the true tissue temperature. Therefore, this method does not reflect the tissue temperature, but represents the temperature of the environment with which the thermocouple is in contact. With the optical temperature determination it is possible to obtain important parameters for the control of the sealing process. Furthermore, the determined temperature can be used as a switch-off/control/adjustment criterion/process parameter and/or for process control/process adjustment.

It has been shown that light preferably of a certain wavelength (for example, white light in the VIS-NIR range) is remitted from the body tissue, wherein the spectrum of light remitted from the body tissue changes as a function of temperature. It is therefore possible to bring an illumination/illumination output for irradiation of body tissue as well as a detector/detector input for detection of light remitted by the body tissue directly to the electrode(s), and thus determine the tissue temperature in the immediate vicinity of (between) the electrode(s) via the detour of the detected remitted light and its spectral distribution.

Accordingly, in the preferred embodiment, a medical instrument (of the HF type) comprises
  at least one instrument branch, which forms at least one energizable electrode for sealing and/or cutting tissue or is arranged in or at the at least one energizable electrode for sealing and/or cutting tissue, wherein the energization of the electrode is controllable and/or adjustable by a calculating unit, and
  at least one temperature measurement device comprising at least one illumination and at least one light detector, each of which is/are (alternately) formed or arranged in or on the at least one instrument branch or in opposite position in/on two instrument branches, and which are in electrical connection with the calculating unit.

Preferably, the medical instrument is a surgical instrument, a monopolar instrument, a bipolar instrument, an electrosurgical instrument, a surgical clip, a surgical clamp, a surgical forceps, surgical scissors, a scalpel, and/or the like. More preferably, the medical instrument is an instrument referred to as a "Seal&Cut" instrument in the trade or marketed under the trademark SEAL&CUT™, which is provided and adapted to cut and simultaneously seal tissue by means of HF technology. Monopolar instruments have the advantage that by being formed in a single shell (only a single instrument branch), a compact design is made possible, and thus lower costs in their manufacture. Bipolar instruments (two opposite instrument branches) have the advantage that a resolved analysis is more feasible, and that they are more variable in the implementation of duplication.

Preferably, the at least one instrument branch is to be understood as the part/the end of a medical instrument, which can be brought into contact with the tissue. More preferably, the at least one instrument branch is a jaw branch. The at least one instrument branch can be formed as an electrode for sealing tissue, preferably the instrument branch here is integrally formed/made of a single part out of a conductive metal or graphite. Alternatively, the electrode can be formed/arranged/embedded in and/or at and/or on the instrument branch, preferably in this case the instrument branch is made out of an insulator and/or electrically insulating material.

Preferably, the medical instrument has two opposing instrument branches, which are preferably movable/pivotable towards each other, at the ends of which facing sides/jaws/areas/instrument branch ends are arranged/formed, which can be brought into contact with the tissue. The instrument branches can themselves be formed as electrodes for sealing tissue. Preferably the instrument branches are made in this case of a conductive metal or graphite, and are insulated from each other. But the electrodes can also be formed/arranged/embedded in and/or at and/or on the instrument branches. Preferably, the instrument branches are in that case made of an insulator and/or electrically insulating material or they are made of metal, and insulated against the electrodes.

Preferably, at least one electrode is controllable and/or adjustable by the calculating unit. More precisely, the current intensity, the voltage, the phase and/or the frequency of the electric current applied to the electrode is controllable or adjustable.

Preferably, the temperature measurement device is an optical temperature measurement device/a thermometer with an optical transmitter in the form of an illumination and an optical receiver in the form of a light detector.

Preferably, illumination means at least one light source/excitation light source and, alternatively, in addition other optical components, such as, for example, a light tunnel comprising optical waveguides/mirrors/lenses/reflecting inner walls/scattering media and the like. More preferably, light source means a white light source/an LED (in the VIS and/or IR and/or UV range), a deuterium lamp (UV range) and/or a halogen lamp (VIS range). In other words, the light at/in/on the instrument branch at the irradiation location/at the at least one entrance opening can be generated directly by means of a light source, or by guiding the light from a light source by means of optical waveguides/mirrors/lenses/light tunnels/scattering media and the like to an irradiation location/a light inlet opening/a light entrance opening of the contact surface of the instrument branch which is provided and adapted to come into contact with the tissue. More preferably, the irradiation of the light of the illumination takes place at a certain angle relative to the tissue contact surface of the corresponding instrument branch and/or electrode, that means that the illumination has an angled/oblique exit opening and/or light radiation in/at/on the instrument branch. In yet other words, the light source itself is arranged obliquely/angled on/at/in the instrument branch or has an oblique/angled surface with respect to the tissue contact surface and/or the light emitting surface. Alternatively, an optical element, such as, for example, a mirror and/or an optical waveguide can be arranged obliquely on/at/in the contact surface (the surface which is provided and adapted to come into contact with the tissue) of the instrument branch and guide the light from the light source to the irradiation site and/or the contact surface.

A white light source, hence, a light source, which emits electromagnetic radiation over the entire VIS range, has the advantage that more information can be obtained from the tissue to be illuminated, as a result of which a tissue identification and/or multivariate data analysis are possible. Furthermore, it is possible to perform a variety of different measurements. For example, on the instrument branch at least one illumination with a white light source and at least one detector can be arranged, which is provided and adapted to measure spectral ranges, preferably with different sensors (Si, InGaAs sensors, etc.).

A light source with a low spectral bandwidth has the advantage that the implementation is simple, that such a light source is inexpensive, that a high temporal scanning can be achieved with such a light source and that distances of more than 2 mm from each other and/or from a detector are possible, since a higher intensity with respect to a certain spectral range is possible.

Preferably, by detector and/or light detector is meant at least one sensor/a photodiode and/or a photomultiplier (PMT) and, if applicable, other optical components, such as, for example, a light tunnel which can comprise optical waveguides/mirrors/lenses//reflective inner walls/scattering media and the like. In other words, the light from the detector/detector part, installed in/at/on the instrument branch, at the remission location can be measured directly by means of a sensor of the detector or the like, located there, at/in/on the instrument branch, or via a light tunnel, which can comprise optical waveguides/mirrors/lenses/reflective inner walls/scattering media and the like, and light can be guided from the contact surface/a light entrance opening of the instrument branch to a sensor or the like, arranged remotely from the contact surface of the instrument branch or even remotely from the instrument branch. More preferably, the irradiation of the light starting from the illumination occurs at a certain angle (0°<angle≤90°) relative to the tissue contact surface of the corresponding instrument branch and/or electrode. More preferably, the detector in/at/on the instrument branch has an entrance opening which is also angled/oblique relative to the contact surface. In yet other words, the detector itself is arranged obliquely/angled on/at/in the instrument branch or has an oblique/angled surface with respect to the tissue contact surface. Alternatively, an optical element, such as, for example, a mirror and/or an optical waveguide can be arranged obliquely on/at/in the contact surface (the surface which is provided and adapted to come into contact with the tissue) of the instrument branch and guide remission light to a remote sensor or the like. The light remitted from the body tissue after irradiation is preferably spectrally resolved into at least two channels (by means of spectrometers, prisms or different filters) and is then detected by the at least two sensors or the like, which contingent thereon are sending at least two signals to the calculating unit/CPU which transforms the at least two signals into a temperature value.

The electrode for sealing tissue is preferably made of metal, conductive ceramic, metallized ceramic, graphite or metallized graphite. The electrode is more preferably formed with a surface which is provided and adapted to reflect electromagnetic radiation.

The calculating unit preferably comprises a processor and a storage medium. The storage medium is provided and adapted to store steps for performing the measurement of the temperature and/or the control and/or adjustment of the current of the electrode.

The calculating unit controls the illumination/light source of the illumination (duration, intensity, wavelength, etc.) by means of a first electrical signal, and the detector detects the light scattered/reflected (exclusively) by the body tissue and/or the remission directly on the tissue to be measured/to be treated (between the instrument branches), and is sending the acquired data as a second electrical signal to the calculating unit. The calculating unit now calculates, by means of an algorithm on the storage medium, the temperature of the tissue which can be derived from the respective second electrical signal. On the basis of the temperature of the tissue calculated in this way, it is calculated online/in real time which current intensity, which voltage and/or frequency the electric current should have which is applied to the at least one electrode.

In addition, in one embodiment, the resistance of the tissue (tissue impedance) can also be determined by the calculating unit, and can be included in the calculation. In other words, the tissue impedance of the tissue at/between the electrodes/sonotrodes can be determined, so that the current intensity, voltage and/or frequency of the electric current applied to the electrode(s) or the US transducer can be controlled or adjusted by the calculating unit in response to the determined tissue impedance and (in combination with) the second signal of the (optical) temperature measurement device.

Preferably, the calculating unit is connected to the (optical) temperature measurement device according to the invention in such a way that the current intensity, the voltage and/or the frequency of the electric current applied to the at least one electrode can be changed in response to the temperature calculated by the calculating unit/CPU, preferably automatically and/or by a predetermined algorithm.

Preferably, the second electrical signal from the detector corresponds to a light spectrum which represents the wavelength and the intensity of the light detected at the detector. On the basis of this spectrum, the shift of the spectral absorption maximum of water is calculated/determined. By means of this shift of the absorption maximum, which is approx. 0.5 nm/K, the temperature can be determined. Since the absorption spectrum of water is characteristic, the shift can also be determined without reference measurement and/or with reference measurement.

Preferably, the calculating unit is configured in such way that it comprises at least one of the following steps or at least one of the following steps is stored on a storage medium in the calculating unit (preferably in the following order):

Controlling the illumination by the calculating unit with a first electrical signal, preferably with an electrical current with a certain current intensity and/or a certain voltage and/or a certain frequency, Emitting an electromagnetic radiation of the illumination (preferably white light) into the tissue in a certain area in the immediate vicinity of an electrode or between two electrodes facing each other, Measuring (by means of the detector) the remission/diffuse reflection of the electromagnetic radiation starting from the body tissue, Sending the measurement results from the detector to the calculating unit by means of a second electrical signal, Transforming the second electrical signal into a tissue temperature value, Preferably determining the tissue impedance, preferably between two electrodes, Processing the tissue temperature value, and preferably the determined tissue impedance by means of the calculating unit, preferably by means of a pre-programmed algorithm on the storage medium, to determine a new current intensity, voltage and/or frequency for the electrical current applied to the electrode(s), in order to reach or approach a temperature of the tissue of above 85° Celsius, preferably above 95° Celsius, and preferably simultaneously of below 110° Celsius, preferably of below 100° Celsius.

Continuously calculating the parameter SP from the continuously determined values Dur95, MeanTempabTmax and E2Tmax;

Providing the switch-off trigger.

In one embodiment, the light tunnel, which is in communication with the light source, can be fed at least one end by at least one light source, and the at least one other end can terminate in the instrument branch. In other words, light from at least one light source can be directed via an optical waveguide or the like to at least one output which is located at/on/in the instrument branch. Alternatively, at least one light source, for example, the LED, can be located/arranged directly on/at/in the instrument branch.

In one embodiment, the light tunnel, which is in communication with the detector, can comprise at least one sensor at at least one end and terminate in the instrument branch at the at least one other end. In other words, light/remission from at least one input, which is located on/in the instrument branch, can be directed to at least one sensor/a photodiode/a photomultiplier or the like via a reflective light channel/an optical waveguide or the like. Alternatively, at least one sensor/photodiode/photomultiplier can be located on/at/in the instrument branch.

Preferably, the illumination and the detector can share one end of a light tunnel. In other words, the beam path of the light source and the beam path of the sensor/photodiode/photomultiplier can share a light tunnel, so that both are in optical contact with the body tissue via a single optical aperture which simultaneously forms the entrance and the exit of the light on/at/in the instrument branch.

Preferably, a plurality of detectors and a plurality of illuminations are arranged on at least one instrument branch. In this regard, the detectors and/or illuminations can each be arranged on an instrument branch in a predetermined pattern. Preferably, the pattern is linear. Alternatively, at least one detector and/or one illumination can be arranged on a first instrument branch, and at least one detector and/or one illumination can be arranged on a second instrument branch, preferably on facing sides of opposite instrument branches. In other words, in this embodiment for bipolar instruments, light can be introduced into the tissue from an illumination device and on an opposite side a detector can measure the light remitted from the tissue.

Preferably, the distance between the at least one illumination and the least one detector is between 0 and 5 mm, more preferably between 0 and 1 mm, since the intensity of the remission is very high in this location.

Preferably, the at least one instrument branch has multiple detectors per illumination, more preferably, the detectors are arranged at equal and/or different distances from the illumination. In other words, the distance from an illumination to a second detector can be greater than the distance to a first detector.

Preferably, the illumination has a discrete light source, preferably with a defined bandwidth, more preferably with a bandwidth smaller than 100 nm.

Preferably, the (optical) temperature measurement device is arranged on a plane of the instrument branch which is located lower than the contact surface of the electrode. In other words, a contact surface of the electrodes and/or the instrument branches, which comes into contact with tissue, forms a plane. This plane is located higher (closer to the tissue) in the contact direction than the plane on which the at least one illumination and/or the at least one detector is arranged.

Preferably, the (optical) temperature measurement device permits a real time/online determination of the temperature during a sealing process/sealing. The online determination is of particular importance for the quality of the sealing. The measurement represents in this case the temperature in the tissue/the tissue temperature and has no latency time or distortion of the measured temperature by the heat capacity of the measuring device, for example, by the heat capacity of electrodes made of metal. The advantage of an optical temperature measurement, which is sensitive to the water in the tissue being grasped/coming into contact is that this temperature measurement device has no significant heat capacity.

Preferably, the remission measurement in the instrument branch and/or in the jaw of an instrument, which may be an instrument referred to as a "Seal&Cut" instrument in the trade or marketed under the trademark SEAL&CUT™, can be performed independently of the position at which the tissue comes into contact with the instrument branch. In other words, the temperature measurement device is arranged in a distributed manner, preferably uniformly distributed, on the surface of the instrument branch in the area which is provided and adapted to come into contact with the tissue. As it has been set forth above, the at least one instrument branch can have a plurality of excitation and detection paths/illumination or detection paths, preferably along and/or in an electrode.

As it is explained above, in addition or alternatively to the measurement of the impedance, a measurement of the temperature shall be performed. The temperature is measured directly in the tissue to be fused, preferably between two opposite instrument branches, and preferably in the (temporal) course of the energization/heating of the tissue. Hereby, the change of the tissue state can be detected directly/online and thus one can also react to it. By extending the algorithm by a further control/adjustment parameter, it is possible to better evaluate the energy input into the tissue, and thus to better control/adjust the fusion of the tissue. In addition, the temperature measurement device according to the invention can also be used to measure other properties of the tissue, for example, the water portion/the water content in the tissue.

Preferably, the electrode has at least a first electrode surface on the surface, which is provided and adapted to come into contact with the tissue. Preferably, the electrode is located on an instrument branch body (in the jaw) of an instrument branch or is formed by the instrument branch. Preferably, at least one light source/at least one light guide/at least one optical component (dichroic mirror/beam splitter/mirror) and/or at least one light detector (or a part thereof) with at least one sensor and, if applicable, a light guide are incorporated in the electrode and/or the instrument branch. A photodiode or a photomultiplier can also be understood as a sensor. Preferably, the electrode has at least one light exit opening from/through which the light of the light source radiates out of the electrode surface and/or into the tissue. Preferably, the electrode has at least one light entrance opening through which the light is radiated/remitted/reflected (exclusively) from the tissue (remission) into/through the electrode surface into the sensor. Preferably, the electrode preferably comprises at least one channel, which is provided and adapted to guide data by means of at least one cable/electrical line to at least one calculating unit, or to conduct light by means of at least one scattering medium/at least one optical waveguide/at least one reflecting surface, to a remote sensor, which in turn guides data by means of at least one cable/electrical line to at least one calculating unit. If the invention has more than one electrode surface and/or more than one instrument branch, the electrode surfaces/instrument branches are spaced apart from each other, preferably in parallel. The space between the electrode surfaces/instrument branches is preferably provided and adapted to receive in an insertable manner a cutting device, such as a knife, a scalpel, an HF scalpel or the like, which is provided and adapted to separate/cut tissue. Thus, on the at least two sides of the cut of the tissue, the electrode/branch surfaces are formed to coagulate the tissue by means of HF technique.

A narrow-band filter is preferably arranged in front of the sensor. A light tunnel may be formed in the electrode and/or the instrument branch. In other words, the light tunnel can guide light through the instrument branch and/or the at least one electrode. All embodiments can be combined with each other.

The task of the invention is solved with respect to a medical instrument according to the invention by the fact that the medical instrument is provided and adapted to perform the method according to the invention. In particular, the medical instrument can comprise a switch-off device/a device for determination a switch-off time, which is provided and adapted for carrying out the method according to the invention.

BRIEF DESCRIPTION OF THE DRAWING FIGURES

The invention is explained in more detail below by means of preferred embodiments with reference to the figures.

FIG. 1 shows an area of an instrument branch according to a first embodiment, FIG. 2 shows a first illumination and detection arrangement of an instrument branch, FIG. 3 shows a second illumination and detection arrangement of an instrument branch, FIG. 4 shows a third illumination and detection arrangement of an instrument branch, FIG. 5 shows an area of an instrument branch according to a second embodiment, FIG. 6 shows the light guidance in the area of the instrument branch according to the second embodiment, FIG. 7 shows an area of an instrument branch according to a third embodiment, FIG. 8 shows the light guidance in the area of the instrument branch according to the third embodiment, FIG. 9 shows an area of an instrument branch according to a fourth embodiment, FIG. 10 shows the light guidance in the area of the instrument branch according to the fourth embodiment, FIG. 11 shows an area of an instrument branch according to a fifth embodiment, FIG. 12 shows the light guidance in the area of the instrument branch according to the fifth embodiment, FIG. 13 shows an area of an instrument branch according to a sixth embodiment, FIG. 14 shows the light guidance in the area of the instrument branch according to the sixth embodiment, FIG. 15 shows an area of an instrument branch according to a seventh embodiment, FIG. 16 shows the light guidance in the area of the instrument branch according to the sixth embodiment, FIG. 17 shows an area of an instrument branch according to an eighth embodiment, FIG. 18 shows the light guidance in the area of the instrument branch according to the eighth embodiment, FIG. 19 shows an area of an instrument branch according to a ninth embodiment, FIG. 20 shows the light guidance in the area of the instrument branch according to the ninth embodiment, FIG. 21 shows an area of an instrument branch according to a tenth embodiment, FIG. 22 shows the light guidance in the area of the instrument branch according to the tenth embodiment, FIG. 23 shows a bipolar instrument branch according to the above embodiments, FIG. 24 shows opposite detectors and illuminations on a bipolar HF instrument, FIG. 25 shows a schematic diagram of a medical device according to the invention, and FIG. 26 shows a schematic diagram of the temperature profile during the process.

The figures are of a schematic type and are intended only to aid understanding of the invention. Identical elements are designated with the same reference numerals. The features of the various embodiments can be exchanged with each other.

DETAILED DESCRIPTION

FIG. 1 shows an area of an instrument branch 1 according to a first embodiment. The instrument branch 1 has at least one electrode 2 which is embedded in the instrument branch 1 in an insulated manner. The electrode 2 has a first electrode surface 4 and a second electrode surface 6 on the branch side which is provided and adapted to come into contact with a body tissue. The electrode(s) 2 is/are located in particular in/on an instrument branch body 8 of the instrument branch 1, which constitutes one half of an operable instrument jaw. Alternating light sources (LEDs) 10 and light detectors and/or sensors 12 are incorporated into the electrode 2 and/or into the instrument branch 1/the instrument branch body 8. The electrode 2 and/or the instrument branch 1/the instrument branch body 8 has light exit openings 14 through which the light from the light source 10 radiates from the electrode surface 4 and/or 6 and/or the branch contact surface into the tissue. The electrode 2 and/or the instrument branch 1/the instrument branch body 8 moreover has light entrance openings 16 through which the light is remitted from the tissue into/through the electrode surface 4 and/or 6 and/or through the branch contact surface into the sensor 12. The electrode 2 and/or the instrument branch 1/the instrument branch body 8 has at least one (longitudinal) channel 18, which is provided and adapted to transmit data/signals from the sensors 12 by means of a cable (not shown in more detail) to a calculating unit (not shown in more detail).

FIG. 2 shows a first variant of an illumination and detection arrangement of instrument branch 1. Each one of the embodiments of the present application can comprise the first illumination and detection arrangement. The upper row of the illumination and detection arrangement of FIG. 2 is arranged/embedded at/in the second electrode/branch surface 6 of FIG. 1. The lower row of the illumination and detection arrangement of FIG. 2 is arranged/embedded at/in the first electrode/branch area 4 of FIG. 1. A detector/sensor 12 and an illumination/light source 10 are each arranged alternately in each row. The dark dots represent a detector/sensor 12 and the light dots represent an illumination/light source 10 here. Preferably, a narrow band (light) filter (not shown) is arranged in front of the detector/sensor 12. More preferably, the optoelectronic components (sensor 12 and illumination 10) are mounted on a circuit board below the electrode/below the tissue contact surface of the branch.

FIG. 3 shows a second variant of an illumination and detection arrangement of an instrument branch. Each one of the embodiments of the present application can comprise the second variant of an illumination and detection arrangement. In this case, the dark dots represent a sensor 12 and the light dots represent a light source 10. The second variant of an illumination and detection arrangement is configured in such a way that that four sensors 12 each are arranged around a light source 10 at an equal distance from the light source 10, wherein the one light source 10 shares two sensors 12 each with another directly adjacent light source. In other words, the/each light source 10 is located in the center of an imaginary rectangle, at the corners of which the sensors 12 are positioned.

FIG. 4 shows a third variant of an illumination and detection arrangement of an instrument branch. Each one of the embodiments of the present application can comprise the third variant of an illumination and detection arrangement. In this case, the dark dots represent a sensor 12 and the light dots represent a light source 10. The third variant of an illumination and detection arrangement is the same as the first variant of an illumination and detection arrangement, except that the row of the illumination and detection arrangement of the second electrode/branch surface begins where the row of the illumination and detection arrangement of the first electrode/branch surface ends.

FIG. 5 shows an area of an instrument branch 101 according to a second embodiment. The instrument branch 101 comprises an electrode 102. The electrode 102 has on the (branch) surface, which is provided and adapted to come into contact with the tissue, a first electrode surface 104 and a second electrode surface 106. In this respect, the branch of the second embodiment corresponds to the branch of the first embodiment. The electrode 102 is located in particular on a distal instrument branch body 108 of the instrument branch 101 which is a portion of an instrument jaw. Light sources 110 and sensors 112 (not shown in detail) are integrated into the instrument branch 101, remote from the tissue contact surface of the instrument branch body 108. The electrode 102/the instrument branch body 108 comprises light exit openings 114 through which the light from the light source (not shown) is directed and from which the light radiates into/enters the tissue from the electrode surface 104 and/or 106 and/or the tissue contact surface of the instrument branch body 108. The electrode 102/instrument branch body 108 comprises light entrance openings 116 through which the light radiates/enters from the tissue into/through the electrode surface 104 and/or 106 and/or tissue contact surface of the instrument branch body 108 into a light tunnel 120 which terminates in the sensor. The light from the light source to the light exit opening 114 is also directed through a light tunnel 120, preferably a different light tunnel 120. The light tunnels 120 are filled with air or another gas or have a vacuum. The light tunnels 120 pass through the instrument branch body 108 and/or through the electrode 102. The, preferably cylindrical, light tunnels 120 have an inner tunnel surface (in hollow cylindrical shape) which in turn has reflective properties for electromagnetic waves (light waves). The tunnel surface on the tunnel inner side is thus provided and adapted to allow total reflection.

FIG. 6 shows the light guidance in the area of the instrument branch/the instrument branch body according to the second embodiment in the light tunnel 120. The incoming light coming from the light source is totally reflected at the inner surface of the light tunnel 120, and can thus be guided through the light tunnel 120. Due to the total reflection on the inner side of the light tunnel 120, the light can also be guided through bent areas/at least one bend or the like. In this case, the light tunnel 120 is guided along the branch body 108 in order to then reach the tissue contact surface of the branch body 108 in a substantially 90° bend (or another angle with respect to the tissue contact surface), where the light tunnel 120 opens.

FIG. 7 shows an area of an instrument branch 201 according to a third embodiment. The instrument branch 201 comprises an instrument branch body 208, which forms a portion of an instrument jaw, which is an electrode or in which an electrode 202 is embedded in an insulating manner, as shown in FIG. 7. The electrode 202 has a first electrode surface 204 and a second electrode surface 206 on the branch surface which is provided and adapted to come into contact with the tissue. Accordingly, the electrode 202 is located on/in the instrument branch body 208 of the instrument branch 201. Light sources and sensors are integrated into the instrument branch 201, remote from the tissue contact surface (not shown). The electrode 202 and/or the instrument branch body 208 has light exit openings 214 through which the light from the light source, which is not shown, is directed and from which the light radiates/enters into the tissue from the electrode surface 204 and/or 206 and/or the tissue contact surface. The electrode 202 and/or the instrument branch body 208 has light entrance opening 216 through which the light radiates/enters from the tissue into/through the electrode surface 204 and/or 206 and/or the tissue contact surface of the instrument branch body 208 into a light tunnel 220 which terminates in a sensor. Light from the light source to the light entrance opening 214 is also directed through a light tunnel 220, preferably a different light tunnel 220. The light tunnels 220 are filled with air or another gas or have a vacuum. The light tunnels 220 pass through the instrument branch body 208 and/or through the electrode 202. The light from the light source is introduced/irradiated perpendicular to the opening of the, preferably cylindrical, light tunnel 220/to the longitudinal direction of the cylindrical light tunnel 220. The light is thus guided straight/in a straight line in the light tunnel 220. To direct the light, at least one mirror and/or a prism is used in the light tunnel 220 in order to deflect/guide the light at a desired angle. The tunnel 220 can take any geometric shape, for example, cylindrical, cuboid-shaped, etc.

FIG. 8 shows the light guidance in the area of the instrument branch according to the third embodiment in the light tunnel 220. The incoming light coming from the light source is fed into the light tunnel 220 in a straight line/in a directional manner/in a parallelly directed manner. Due to guidance by means of at least one mirror in the light tunnel 220, the light can also be guided over angled areas/angles or the like.

FIG. 9 shows an area of an instrument branch 301 according to a fourth embodiment. The instrument branch 301 has an electrode 302, which is received in an instrument branch body 308, which forms a tissue contact surface. The electrode 302 has a first electrode surface 304 and a second electrode surface 306 on the surface which is provided and adapted to come into contact with the tissue. Thus, the electrode 302 is located in/on the instrument branch body 308 of the instrument branch 301. In the instrument branch 301, light sources and sensors (not shown) are provided remotely from the tissue contact surface of the instrument branch body 308. The electrode 302 and/or instrument branch body 308 has light exit opening 314 through which the light from the light source, which is not shown, is directed and from which light radiates into/enters the tissue from the electrode surface 304 and/or 306 and/or the instrument branch body 308. The electrode 302 and/or the instrument branch body 308 has light entrance openings (not shown) through which the light radiates/enters from the tissue in/through the electrode surface 304 and/or 306 and/or through the contact surface of the instrument branch body 308 into a light tunnel 320 which terminates in a sensor. The light from the light source to the light exit opening 314 is also directed through a, preferably different, light tunnel (not shown). The light tunnels 320 are filled with a diffusing bulk material 322. The light tunnels 320 pass through the instrument branch body 308 and/or through the electrode 302. In this embodiment, at least two light tunnels 320 are arranged in parallel in the electrode 302 and/or the instrument branch body 308 in a row/line such that a row of light entrance openings 314 and light exit opening (not shown) are each provided in a respective electrode surface 304 and 306. In an embodiment not shown, the bulk material of the fourth embodiment can itself be a light source, that means that the bulk material can glow.

FIG. 10 shows the light guidance in the area of the instrument branch according to the fourth embodiment in a light tunnel 320. The incoming light coming from the light source is fed into the light tunnel 320, more specifically into the diffusing and/or luminous bulk material 322 in the light tunnel 320. Due to the scattering of the light in the bulk material 322, the light is radiated into the tissue and the remitted light is guided/scattered to the sensor by another light tunnel (not shown) having the same structure.

FIG. 11 shows a portion of an instrument branch 401 according to a fifth embodiment. The instrument branch 401 has an electrode 402 which is in this case embedded in an instrument branch body 408 in an insulating manner. The electrode 402 has on the surface of the instrument branch body 408, which is provided and adapted to come into contact with the tissue, a first electrode surface 404 and a second electrode surface 406. Thus, the electrode 402 is located in/on the instrument branch body 408 of the instrument branch 401. In the instrument branch 401, light sources and sensors are provided remotely from the tissue contact surface of the instrument branch body 408 (not shown). The electrode 402 and/or the instrument branch body 408 comprises light exit openings 414 through which the light from a light source, which is not shown, is directed and from which light radiates into/enters the tissue from the electrode surface 404 and/or 406 and/or from the tissue contact surface. The electrode 402 and/or the instrument branch body 408 has light entrance openings (not shown) through which the light from the tissue radiates/exits in/through the electrode surface 404 and/or 406 and/or through the tissue contact surface into a light tunnel 420 which terminates in a sensor. The light from the light source to the light exit opening 414 is also directed through a, preferably different, light tunnel (not shown). The light tunnels 420 are filled with a textured bulk material 422. The light tunnels 420 pass through the instrument branch body 408 and/or through the electrode 402. In this embodiment, at least two light tunnels 420 are arranged in parallel in the electrode 402 and/or the instrument branch body 408 in a row/line, such that a row of light entrance openings 414 and light exit openings (not shown) are each provided in a respective electrode surfaces 404 and 406. In an embodiment not shown, the bulk material of the fifth embodiment can itself constitute a light source, that means, the bulk material can glow.

FIG. 12 shows the light guidance in the area of the instrument branch according to the fifth embodiment in a light tunnel 420. The incoming light coming from the light source is fed into the light tunnel 420, more specifically into the structured bulk material 422 in the light tunnel 420. Due to the structure of the insert in the bulk material 422, the light is radiated into the tissue and the remitted light is guided/scattered to a sensor by another light tunnel (not shown) having the same structure.

FIG. 13 shows an area of an instrument branch 501 according to a sixth embodiment. The instrument branch 501 has an electrode 502, wherein in this embodiment, the instrument branch body 501 and the electrode 502 correspond to the previous embodiments in terms of their structure and arrangement. Light sources and sensors (not shown) are integrated into the instrument branch body. The electrode 502/the instrument branch body has light exit openings 514 through which the light from a light source, which is not shown, is directed and from which the light radiates into/enters the tissue. The electrode 502/the instrument branch body comprises light entrance openings (not shown) through which the light from the tissue radiates/enters into a light tunnel 520 which terminates in a sensor. The light from the light source to the light entrance opening 514 is directed through at least one light tunnel 520. In this embodiment, a single light tunnel 520 is formed in the electrode 502 and thus in the instrument branch body 501. A row each of light exit openings 514 and light entrance openings (not shown) is provided in the electrode 502 and/or in the instrument branch body. At least one mirrored/reflective oblique/angled plane 524 is formed in the light tunnel 520. The plane 524 can be formed by polishing the electrode and/or instrument branch body, or by introducing a mirror into the light tunnel 520. The light tunnel 520 passes through the instrument branch body. At least one row of light exit openings 514 and light entrance openings (not shown) is provided in a surface of the electrode 502/the instrument branch body. Alternatively or in addition, a single light tunnel 520 of this type can serve for both excitation and reception of reflected light— with the appropriate filters. This means that a filter, which corresponds to the remission wavelength range, is placed after the light source, but the remaining light is directed into the tissue and is received by the same and/or an adjacent opening, and returned to the sensor via the same reflective plane 524.

FIG. 14 shows the light guidance in the area of the instrument branch 501 according to the sixth embodiment in the light tunnel 520. The incoming light coming from the light source is fed into the light tunnel 520 and is deflected at the angled mirroring plane 524 at a predetermined angle (preferably with an angle between 0° and 90°). The light is radiated into the tissue through the mirror(s)/mirroring surface(s)/mirroring plane(s) 524, and the remitted light is directed/guided to a sensor by another light tunnel (not shown) having the same structure.

FIG. 15 shows an area of an instrument branch 601 according to a seventh embodiment. The instrument branch 601 has an electrode 602 which is received by an instrument branch body 608. The electrode 602 has a first electrode surface 604 and a second electrode surface 606 on the surface of the instrument branch body 608 which is provided and adapted to come into contact with the tissue. Light sources and sensors (not shown) are integrated into the instrument branch body 608. The instrument branch body 608 comprises light exit openings 614 through which the light from a light source, which is not shown, is directed and radiates into/enters the tissue from the tissue contact surface. Furthermore, the instrument branch body 608 comprises light entrance openings (not shown) through which the light radiates/enters from the tissue into/through the tissue contact surface of the instrument branch body 608 into a light tunnel 620 which terminates in a sensor. The light from the light source to the light exit opening 614 is also directed through a second light tunnel (not shown). At least one partially translucent plane 626 is introduced into the light tunnel 620, which transmits a portion of an electromagnetic radiation, hence is translucent for a portion of the light, and reflects a portion of the light. Preferably, the partially translucent plane is a partially translucent mirror, and more preferably, a plurality of partially translucent planes 626 are arranged in series in the light tunnel.

FIG. 16 shows the light guidance in the area of the instrument branch 601 according to the seventh embodiment in a light tunnel 620. The incoming light coming from the light source is fed into the light tunnel 620. The incoming light coming from the light source is fed into the light tunnel 620 in a straight line/in a directional manner/in a parallelly directed manner. By guiding by means of at least one partially translucent mirror 626 in the light tunnel 620, the light is guided/reflected/mirrored over angled regions/angles or the like. The light passing through a partially translucent mirror 626 is incident on another partially translucent mirror 626, which is arranged at the same angle as that of the previous mirror, and so on. Through the partially translucent mirror/mirroring surface/mirroring plane 626, the light is radiated into the tissue and the remitted light is directed/guided to a sensor by another light tunnel (not shown) having the same structure.

FIG. 17 shows an area of an instrument branch 701 according to an eighth embodiment. The instrument branch 701 comprises an electrode 702. The electrode 702 is located on an instrument branch body 708 of the instrument branch 701. In the instrument branch 701, light sources and sensors are provided remotely from the instrument branch body 708, preferably externally (not shown). The instrument branch body 708 comprises at least one light tunnel 720 through which light of the light source, which is not shown, is directed and from which light radiates into/enters the tissue. The instrument branch body 708 comprises at least one other light tunnel 720 through which the light from the tissue is directed to a sensor. In this embodiment, the light tunnels 720 are formed by optical waveguides, such as, for example, optical fibers.

FIG. 18 shows the light guidance in the area of the instrument branch according to the eighth embodiment in a light tunnel 720. The incoming light coming from the light source is totally reflected at the inner surface of the light tunnel 720, and can thus be guided through the light tunnel 720. Due to the total reflection at the inner side of the light tunnel 720, the light can also be guided through bent areas/at least a bend or the like.

FIG. 19 shows an area of an instrument branch 801 according to a ninth embodiment. The instrument branch 801 comprises an electrode 802. The electrode 802 has a first electrode surface 804 and a second electrode surface 806 on the tissue contact surface of its instrument branch body, which is provided and adapted to come into contact with the tissue. Light sources and sensors (not shown) are incorporated in the instrument branch body. The instrument branch body also comprises light exit openings 814 through which the light from a light source, which is not shown, is guided and radiates into/enters the tissue. The instrument branch body also includes light entrance openings 816 through which the light from the tissue in/through the instrument branch body radiates into/enters a light tunnel 820 which terminates in a sensor. Light from the light source to the light exit opening 814 is directed through the same light tunnel. In other words, light exit openings 814 can act as light entrance openings 816 and vice versa. At least two partially translucent planes 626 are introduced into the light tunnel 820, which transmit a portion of an electromagnetic radiation, hence, are translucent for a portion of the light, and reflect a portion of the light. Preferably, the partially translucent plane is a partially translucent mirror, and more preferably, a plurality of partially translucent planes 626 are arranged in series in the light tunnel. Due to this arrangement in this embodiment, a partially translucent mirror each is assigned to each of a light exit opening 814 or a light entrance opening 816.

FIG. 20 shows the light guidance in the area of the instrument branch 801 according to the ninth embodiment in a light tunnel 820. The incoming light coming from the light source is fed into the light tunnel 820. The incoming light coming from the light source is fed into the light tunnel 820 in a straight line/in a directional manner/in a parallelly directed manner. By guiding by means of at least two partially translucent mirrors 826 in the light tunnel 820, the light is guided/reflected/mirrored over angled areas/angles or the like. The light passing through a partially translucent mirror 826 is incident on at least one other partially translucent mirror 826, which is arranged at the same angle as the previous mirror, and so on. Through the partially translucent mirror/mirroring surface/mirroring plane 826, the light is irradiated into the tissue and the remitted light is directed/guided from the same light tunnel 820 but through an adjacent opening to a sensor. In yet other words, an opening is both a light exit opening and a light entrance opening for an adjacent opening.

FIG. 21 shows an area of an instrument branch 901 according to a tenth embodiment. The instrument branch 901 comprises an electrode 902, wherein in this embodiment, the instrument branch body as well as the electrode correspond to the previous embodiments in terms of their structure and arrangement. Accordingly, in the instrument branch, light sources and sensors (not shown) are provided remotely from the tissue contact surface of the instrument branch body. The instrument branch body includes light exit openings 914 through which the light from a light source, which is not shown, is directed and from which the light radiates into/enters the tissue. The instrument branch body further includes light entrance openings 916 through which the light from the tissue radiates/exits into a light tunnel 920 which terminates in a sensor. The light from the light source to the light exit opening 914 is directed through at least one light tunnel 920. The light from the light entrance opening 916 to the sensor is directed through at least one other light tunnel 920 (of the same design). Thus, in this embodiment, at least two light tunnels 920 are formed in the instrument branch body. The light exit opening(s) 914 and light entrance opening(s) 916 are alternately provided in the instrument branch body. At least one mirrored/reflective oblique/angled plane 924 is formed in the light tunnel 920.

FIG. 22 shows the light guidance in the area of the instrument branch 901 according to the tenth embodiment in the light tunnel 920. The incoming light coming from the light source is fed into the light tunnel 920, and deflected at the angled mirroring plane 924 at a predetermined angle (preferably with an angle between 0 and 90°). Through the mirror/mirroring surface/mirroring plane 924, the light is irradiated into the tissue, and the remitted light is directed/guided to a sensor by another light tunnel 920 having the same structure.

FIG. 23 shows a bipolar instrument branch according to the above embodiments. The embodiments one through ten are provided and adapted to be used in a bipolar medical HF instrument, wherein two instrument branch bodies are preferably pivotally mounted relative to each other, and define a tissue receiving gap between each other.

FIG. 24 shows opposing detectors and illuminations on a bipolar HF instrument. In this case, the light exit openings 1014 of the illuminations and the light entrance openings 1016 of the detectors are respectively located on opposing instrument branches/instrument branch bodies.

FIG. 25 shows a schematic diagram of a medical device 1100 according to the invention. A light source 1110 is provided and adapted to emit light. A sensor 1112 is provided and adapted to detect light. The light source emits the light through a light exit opening 1114. The sensor 1112 receives the light through a light entrance opening 1116. The light sources 1110 and the sensors 1112 are in communication with data lines 1130 and 1132 which are located in a channel 1118. The channel 1118 is formed in an instrument branch body which also receives the electrodes in an insulating manner. The one instrument branch body, in which the electrode 1134 is received, clamps the tissue 1138 with an instrument branch body in which the opposite electrode 1136 is received. The electrode 1134 and the electrode 1136 are in communication with the lines 1140 and 1142. The data lines 1130 and 1132 as well as the lines 1140 and 1142 are in communication with a calculating unit 1144 which comprises a storage medium 1146.

FIG. 26 shows a schematic diagram of a temperature profile during the process. Here, the temperature v of the tissue is plotted on a graph over time t. t1 marks the point in time at which the tissue reaches the temperature of 85° Celsius, preferably 95° Celsius. T2 marks the point at which the value SP reaches a value of 2.5. The value SP has been calculated online from the point in time when the temperature of the tissue has reached 85° Celsius, preferably 95°. From this point in time, the duration for which the temperature of a tissue is above 85° Celsius, preferably above 95° Celsius, was measured, and the average temperature was calculated online as from the first time when 85° Celsius, preferably 95° Celsius were reached (shown here by the dashed line). These two values are multiplied in real time and divided by the energy input until 85° Celsius, preferably 95° Celsius are reached, thereby calculating the value SP, preferably in real time.

The invention claimed is:

1. A method for determining a switch-off time of a medical instrument, comprising the steps of:
measuring a duration for which a temperature of a tissue is above a threshold value of at least 85° Celsius;
calculating a mean temperature as from a first time when the temperature of the tissue reaches the threshold value of at least 85° Celsius;
measuring and/or calculating an energy input until the temperature of the tissue reaches the threshold value of at least 85° Celsius;
calculating a parameter SP, which links the duration, the mean temperature and the energy input; and
switching off the medical instrument at a predetermined value of the parameter SP,
wherein the parameter SP is a result from a duration for which the temperature of the tissue is above the threshold value of at least 85° Celsius, multiplied by the mean temperature as from the first time when the temperature of the tissue reaches the threshold value of at least 85° Celsius, divided by the energy input until the temperature of the tissue reaches the threshold value of at least 85° Celsius.

2. The method according to claim 1, wherein the method further comprises the steps of:
emitting light with an excitation spectrum into of the tissue by at least one illumination;
receiving a remission of light with a remission spectrum from the tissue by at least one detector;
converting the remission spectrum into a detector signal with the at least one detector;
sending the detector signal to a calculating unit,
calculating the remission spectrum from the detector signal with the calculating unit,
calculating an absorption spectrum of the tissue by comparing the excitation spectrum with the remission spectrum using the calculating unit,
calculating at least one absorption maximum from the absorption spectrum using the calculating unit; and
calculating a temperature in the tissue by comparing the at least one absorption maximum with at least one reference using the calculating unit.

3. The method according to claim 2, wherein the method further comprises the step of:
storing at least one reference as an absorption maximum at a certain temperature in a storage medium in the calculating unit.

4. The method according to claim 2, wherein the method further comprises the step of:
applying the at least one illumination and the at least one detector to the tissue.

5. The method according to claim 2, further comprising the step of:
controlling and/or adjusting and/or switching off a medical instrument using the calculating unit based on the mean temperature and/or a tissue impedance.

6. The method according to claim 5, wherein the controlling and/or adjusting and/or switching off takes place when a predetermined temperature is reached at a temperature that is greater than the threshold value of at least 85° Celsius.

7. The method according to claim 5, wherein the controlling and/or adjusting and/or switching off of the medical instrument takes place in real time.

8. The method according to claim 2, wherein the at least one detector is adapted to measure remission spectra in the NIR range of 1000 nm to 1700 nm.

9. The method according to claim 2, wherein the at least one illumination and the at least one detector are spaced apart.

10. The method according to claim 1, wherein temperature measurement is performed during a sealing process.

11. A storage medium of a medical instrument, wherein the steps of claim 1 are stored on the storage medium.

12. A medical instrument for sealing and/or cutting of tissue, the medical instrument comprising:
a temperature measurement device adapted to measure a temperature of a tissue; and
a calculating unit, wherein the medical instrument is adapted to measure a duration for which the temperature of the tissue is above a threshold value of at least 85° Celsius, wherein the calculating unit is adapted to calculate a mean temperature as from which the temperature of the tissue reaches the threshold value of at least 85° Celsius for the first time, wherein the medical instrument is further adapted to measure and/or to calculate an energy input until the temperature of the tissue reaches the threshold value of at least 85° Celsius, wherein the calculating unit is adapted to calculate a parameter SP which links the duration, the mean temperature and the energy input, wherein the medical instrument is adapted to switch off at and/or as a result of the parameter SP reaching a predetermined value, and wherein the parameter SP is a result from a duration for which the temperature of the tissue is above the threshold value of at least 85° Celsius, multiplied by the mean temperature as from the first time when the temperature of the tissue reaches the threshold value of at least 85° Celsius, divided by the energy input until the temperature of the tissue reaches the threshold value of at least 85° Celsius.

13. The medical instrument according to claim 12, further comprising at least one instrument branch that forms at least one energizable electrode for sealing and/or cutting of tissue, or is arranged in or on the at least one energizable electrode, wherein energization of the at least one energizable electrode is controllable and/or adjustable by the calculating unit.

* * * * *